United States Patent [19]

Ellman et al.

[11] Patent Number: 5,571,101
[45] Date of Patent: Nov. 5, 1996

[54] ELECTROSURGICAL ELECTRODE FOR DCR SURGICAL PROCEDURE

[76] Inventors: Alan G. Ellman; Jon C. Garito, both of 1135 Railroad Ave., Hewlett, N.Y. 11557

[21] Appl. No.: 450,703

[22] Filed: May 25, 1995

[51] Int. Cl.$^6$ .................................................. A61B 17/39
[52] U.S. Cl. ................................................. 606/45; 606/49
[58] Field of Search ................................. 606/44, 45, 46, 606/49

[56] References Cited

U.S. PATENT DOCUMENTS

| | | | |
|---|---|---|---|
| 1,841,968 | 1/1932 | Lowry | 606/45 |
| 4,593,691 | 6/1986 | Lindstrom | 606/49 |

FOREIGN PATENT DOCUMENTS

| | | | |
|---|---|---|---|
| 896711 | 3/1945 | France | 606/44 |
| 2851239 | 3/1980 | Germany | 606/45 |
| 2227415 | 8/1990 | United Kingdom | 606/44 |

OTHER PUBLICATIONS

Ann Otol Rhinol Laryngol, vol, 103. pp. 363–366, 1994.

*Primary Examiner*—Lee S. Cohen

[57] ABSTRACT

An electrode for use in an electrosurgical nasal procedure for excising tissue. The procedure is known as DCR. In a preferred embodiment, the electrode is characterized by a bare active tip portion terminating a transversely-extending portion from an electrode shaft. The tissue excising is effected with the bare tip and the adjacent portions of the transversely-extending portion and electrode shaft are made insulating to prevent accidental burns to the patient and to allow the physician to use these insulated parts to help position and guide the active tip portion during the surgical procedure.

8 Claims, 3 Drawing Sheets

5,571,101

ELECTROSURGICAL ELECTRODE FOR DCR SURGICAL PROCEDURE

This invention relates to an electrosurgical electrode for dacryocystorhinostomy (DCR).

BACKGROUND OF THE INVENTION

DCR is a surgical procedure for correction of obstruction of the lacrimal system. The known treatments for these disorders include surgical excision of certain obstructing tissue of the patient by an external, endoscopically-controlled, intranasal procedure with scalpel incisions made through the lower eyelid. See, for example, Ann Otol Rhinol Laryngol, Vol. 103, pgs. 363–366, 1994. This procedure causes a cutaneous scar, cosmetic blemish, surgical trauma, and excessive bleeding. Additional disadvantages of the external DCR procedure are lengthened recovery time and extended post-operative pain.

With the advent of the laser and its application in endoscopic/laporoscopic procedures, surgeons began to use the laser for DCR. The major shortcomings of the laser are that it is very expensive, time-consuming to set up, and requires many weeks of training in its use. A clinical disadvantage is that use of the laser results in a high degree of tissue destruction, which results in delayed healing and post-operative pain.

SUMMARY OF THE INVENTION

An object of the invention is an improved DCR surgical procedure.

We have invented a novel electrode for use in an electrosurgical DCR procedure. This electrosurgical procedure using our novel electrode enables physicians to offer to patients a treatment that is efficiently performed, easily learned and thus performed at a significantly reduced price, and with less tissue damage and superior results compared to procedures done with a scalpel or a laser.

The procedure using our novel electrode is based on the incising of an area of the nasal mucosa anterior to the middle turbinate approximately 15–20 mm in diameter by intranasal electrosurgery, i.e., via the nasal passageway. The electrode of the invention is uniquely configured to enable the active tip to reach and incise the extremely vascular nasal mucosa (delicately endonasally) while avoiding damage to surrounding tissue.

In a preferred embodiment, our novel electrode is characterized by a bare active tapered tip portion extending at a substantially right angle to an insulated electrode shaft. The tissue excising is effected with the bare tip moved by the surgeon in a generally circular path, and the adjacent portions of the tip support and electrode shaft are made insulating to prevent accidental burns to the patient and to allow the physician to use these insulated parts to help position and guide the active tip portion during the surgical procedure. The electrosurgical procedure has the important advantages of being able to cut the tissue while at the same time coagulating the cut tissue causing minimum bleeding. It is preferred that the electrosurgical currents used be above 2 MHz, and preferably above 3 MHz. At these high frequencies, commonly referred to as radiosurgery, cutting is accomplished by volatilizing intracellular fluids at the point of the transmitting electrode contact which is primarily responsible for only small lateral heat spread and thus less damage to neighboring cell layers.

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in which there are illustrated and described the preferred embodiments of the invention, like reference numerals or letters signifying the same or similar components.

DETAILED DESCRIPTION OF THE PREFERRED EMBODIMENTS

Figure 1:
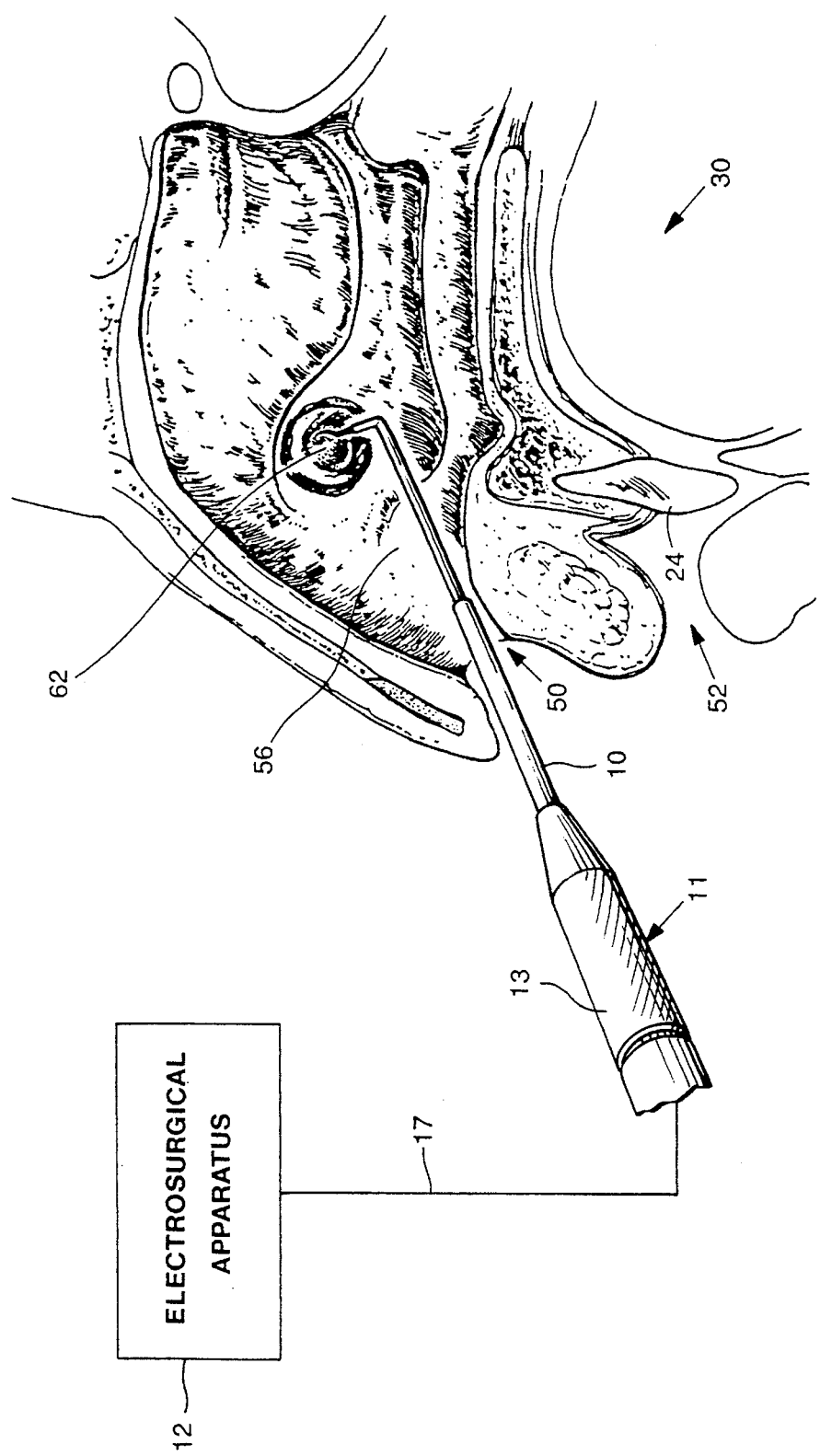
FIGS. 1 and 2 are perspective views showing how the electrodes of FIGS. 4–10 are used in a surgical procedure in accordance with the invention.

FIG. 1 illustrates a preferred form of the novel electrosurgical electrode 10 of the invention mounted in a standard handpiece 11 (only the front end of which is shown) which is connected in the conventional manner to conventional electrosurgical apparatus 12. As an example only, and not meant to be limiting, the handpiece can be a model H6 Surgitron handpiece available from Ellman International, Inc. of Hewlett, N.Y., and the electrosurgical apparatus can be model AAOP Surgitron FFPF available from the same supplier. The Ellman equipment is preferred due to its high operating frequency, typically at 3.8 MHz. Such handpieces 11 conventionally comprise an electrically insulating pen-like member 13 having an electrically conductive tube (not shown) running lengthwise through it and configured to receive the bare metal shaft of the electrosurgical electrode 10. Not shown are the conventional collet type fittings at the handpiece front end to hold the metal shaft in position and to establish the desired electrical connection thereto. The opposite end of the electrically conductive tube is connected by way of a cable 17 to the electrosurgical apparatus 12. Also connected to the latter is the usual indifferent plate (not shown) which during use is in contact with the patient's body. When the electrosurgical apparatus is energized, high frequency electrosurgical currents are generated which are coupled by way of the electrically conductive tube of the handpiece to the electrode 10. The physician, in the usual way, holds the handpiece while applying the working end of the electrode to the desired area of the patient to be treated.

Figure 4:
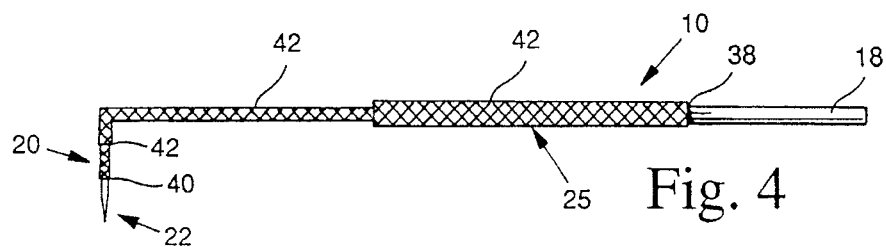
FIG. 4 is a side view of one form of ENT electrode of the invention.
Figure 5:
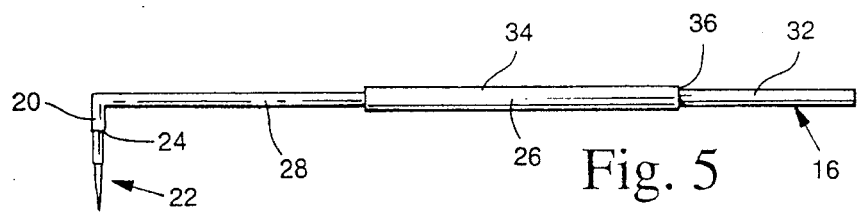
FIG. 5 is a view similar to FIG. 4 of the electrode minus its insulation coatings.

In accordance with the present invention, as illustrated in FIG. 4, the electrosurgical electrode comprises a straight shaft 16 having at one end, the right end, a bare portion 18 to provide a good electrical connection to the handpiece, and at the opposite or working end a transversely-extending portion 20 terminating in a bare tapered tip 22 serving as the active electrode portion. The shaft 16 is constituted preferably of a thin metal tube, for example of brass, and the active tip 22, which is solid metal, for example also of brass, is brazed or welded to to the tube end 24. The active tip 22 is electrically connected to the shaft 16 and any electrosurgical currents conveyed to the shaft are in turn available at the active tip 22. FIG. 5 shows the shape of the electrode 10 during an intermediate step in its manufacture when it is constituted solely of metal.

In accordance with a feature of the invention, the shaft portion is constituted of a relatively large diameter section 26 followed by a relatively small diameter section 28 which extends into the transversely-extending portion 20 and terminates at the bare active tip portion 22. Preferably but not essentially, the shaft portion is divided into a slightly smaller section 32 at the right end and a slightly larger middle section 34 forming a shoulder 36 which can conveniently act as a stop when the electrode is inserted into the handpiece. A typical size of the bare end section is 0.063 inches for fitting to a standard handpiece, and the larger middle section can vary between 0.08–0.20 inches, which is not critical. A more significant dimension is the diameter of the small diameter section 28, as this part extends deeply into the nasal passageway. A preferred diameter is 0.03–0.06 inches.

The transversely-extending portion 20 can range from about 0.28–0.55 inches in length, with a bare active tip ranging from about 0.05–0.30 inches in length. The active tip has a range of dimensions in order to perform the procedure on patients requiring the excision of different sizes of tissue. For smaller excisions, a length of about 0.05–0.20 inches is preferred. For larger excisions, a length of about 0.11–0.30 inches is preferred.

In accordance with a further feature of the invention, the portion 25 extending from its free end 38 adjacent the handpiece 11 to the active tip close to but spaced from its end, referenced 40, is covered with a coating 42 of an electrically insulating material, which may be one of many suitable electrically insulating plastics, baked Teflon being one example. The insulating coating 42 extends from the larger middle section 26 along the smaller section 28 at the left and continues into the transversely-extending portion 20 to point 40, about one-half the distance to the bare tip 22 in the FIG. 4 embodiment.

Figure 7:
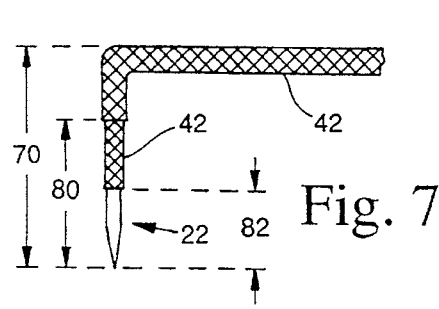
FIGS. 7–10 are side views of different active end portions of electrodes in accordance with the invention.

FIGS. 4 and 7 show this more clearly. The electrically insulating coatings 42 are shown here, for clarity, in double hatched and stipled form.

Figure 2:
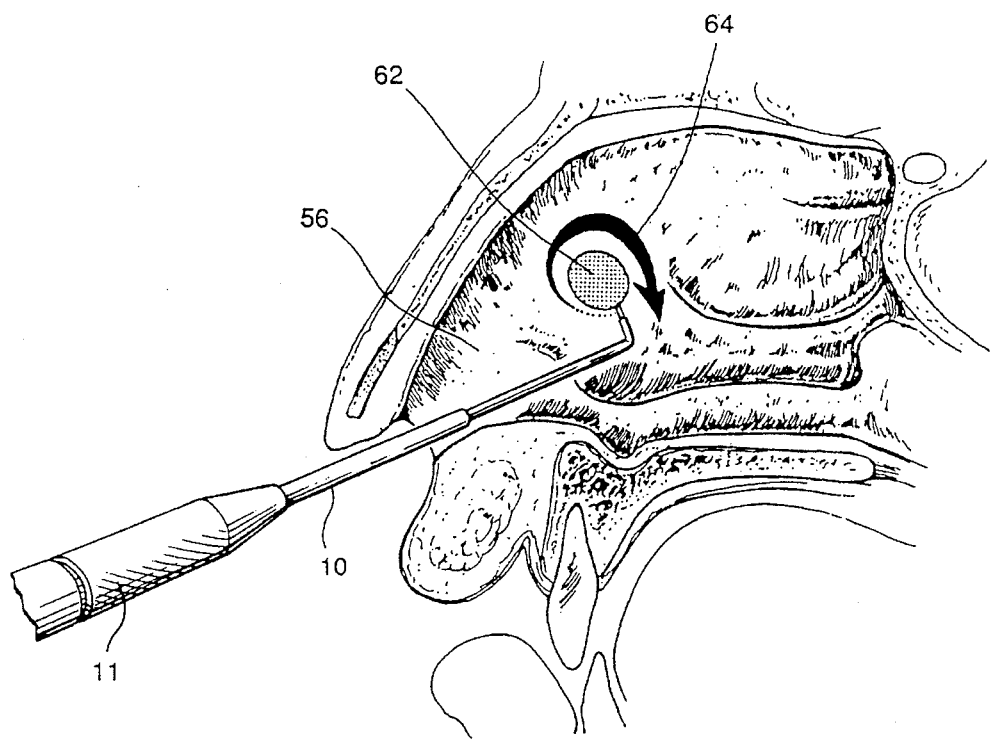
Figure 3:
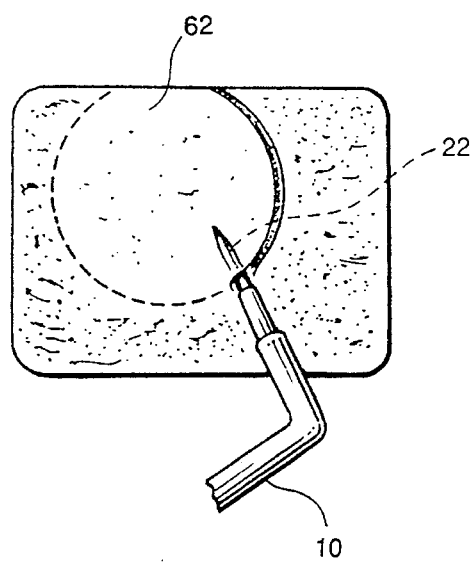
FIG. 3 is a detail view, also in perspective, of the procedure.

The reasons for the electrode shape will be clearer from a description of one form of the surgical procedure with reference to FIGS. 1–3, which show a cross section of a patient 30 with a nose opening 50, a mouth 52 and teeth 24 in bone. Another structural feature is the nasal passageway 56.

After the patient with nasalacrimal duct obstruction has been pre-medicated with an appropriate oral analgesia and placed in a seating position under local anesthesia, the surgeon extends the handpiece-held electrode through the nasal passageway 56, turns on the electrosurgical apparatus 12, and by applying the instrument 10 as shown realizes with the active tip 22 incision and coagulation of a delicate area 62 of nasal mucosa. As shown with greater detail in FIGS. 2 and 3, the bare point 22 of the electrode 10 enters the tissue and is then swept by the surgeon in a generally circular path shown by the arrow 64 to surgically remove the tissue region 62. Subsequently, a portion of the underlying bone can be removed if desired. The nasal mucosa is extremely vascular and an important advantage of its removal electrosurgically is simultaneous coagulation of the cut blood vessels which minimizes bleeding and trauma.

The shape of the electrode, with a generally long, axially-oriented, main portion and with a short generally transverse active portion, shorter in length than the size of the typical nasal passageway, makes it relatively easy to insert the electrode and reach the nasal mucosa region desired and move the instrument in the required circular path to excise the desired tissue region. The insulating coatings 42 are essential to prevent accidental burning or other tissue damage by the sides of the electrode as the instrument is manipulated through the nasal passageway.

Figure 6:
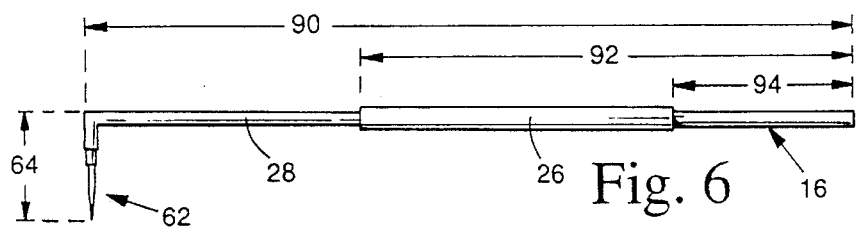
FIG. 6 is a view similar to FIG. 5 of another form of ENT electrode of the invention.

Due to different patient sizes and shapes, a family of electrodes is necessary to perform the procedure on a wide variety of patients. FIG. 6 shows a different shape of the electrode before coating with insulating material. In this instance, the overall length 64 of the transverse portion is about the same as that of the FIG. 5 electrode, but the bare pointed end 62 is longer.

Figure 9:
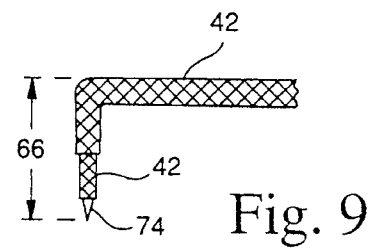
Figure 8:
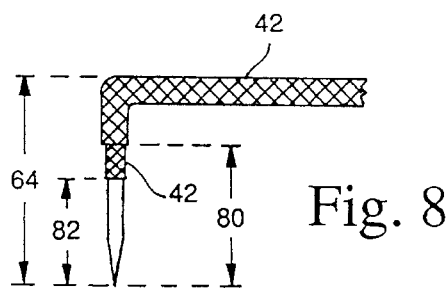
Figure 10:
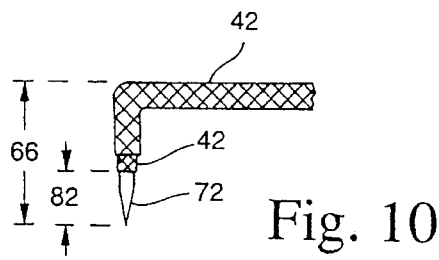

FIGS. 7–10 show the active ends of a typical family of DCR electrodes according to the invention. The electrode end in the FIG. 7 embodiment is approximately the same as that of the FIG. 4 embodiment, whereas the FIG. 8 embodiment is similar to that of FIG. 6. FIGS. 9 and 10 show embodiments for smaller persons. Note that the overall length 66 of the transverse portion is shorter than that 70 of the FIG. 7 embodiment or of 64 in the FIG. 8 embodiment. The bare point 74 in the FIG. 9 embodiment is the shortest of all, and the bare point 72 in the FIG. 10 embodiment is somewhat longer.

The three most significant dimensions are (1) the overall length of the transverse portion, 64, 66, 70, (2) the length 80 from the tip to where the solid needle end is connected to the tubular part, and (3) the length 82 of the bare point. The preferred range of dimensions of the lengths 64, 66, 70 is about 0.28–0.55 inches, with about 0.294 or 0.437 inches preferred; the preferred range of dimensions of the length 80 is about 0.14–0.45 inches, with about 0.156 or 0.30 inches preferred; the preferred range of dimensions of the bare tip length 82 is about 0.05–0.30 inches, with the range of about 0.062–0.240 inches preferred.

The length of the axially aranged part is also important, and those dimensions, indicated at at 90, 92 and 94 preferably range from about 2.77–3.07 inches for length 90, about 1.78–1.97 inches for length 92, and about 0.65–0.73 inches for length 94. Thus, length of the electrically-insulated coated part of the shaft is about 2.04–2.42 inches, which is arrived at by subtracting the range length of the bare part indicated at 94 from the overall range length indicated at 90.

With the Ellman equipment, the fully rectified or cut/coag current is used at a power setting of about 3–4 with the active bare tip electrode 22. There is very little trauma and the sore nasal area felt by the patient is easily handled by analgesia and anti-inflammatory drugs.

From FIG. 4 it will be clear that the electrically insulating coatings on the shaft 16 and the initial portion of the transversely-extending portion 20 function to prevent undesired contact and possible burns by those members to adjoining and surrounding tissue.

The procedure described can be effective in reducing the effects of these disorders, and offers the advantages of avoiding the use of expensive lasers, hospitalization, and much patient trauma, pre-surgery and post-surgery.

As examples of suitable short and deep electrodes, which is not meant to be limiting, the length of the shaft 16 was about 2.9 inches, the length of the transversely-extending portion 20 about 0.294 or 0,437 inches; for the short electrode, suitable lengths of the bare wire tip was 0.062 or 0.171 inches long; for the deep electrode, suitable lengths of the bare wire tip was 0.125 or 0.240 inches long. It will be appreciated that the length of the tapered bare wire end 22 controls the depth of the incision made by the electrode as illustrated in FIG. 3.

It will also be understood that the electrode of the invention is not limited to its use for endoscopic nasal surgery via intranasal access to paranasal structures including the sinuses and lacrimal sac, and in particular intranasal DCR. To those skilled in this art, there will certainly be other uses for this novel electrode that provides an active wire tip arranged generally transverse to the shaft, with the adjacent electrode sections coated with insulating material for accurately guiding and controlling the position of the active tip during a tissue excising electrosurgical procedure.

While the invention has been described in connection with preferred embodiments, it will be understood that modifications thereof within the principles outlined above will be evident to those skilled in the art and thus the invention is not limited to the preferred embodiments but is intended to encompass such modifications.

What is claimed is:

1. An electrosurgical electrode for excising of nasal tissue, comprising:
   (a) an electrically conductive shaft member having a first exposed end for mounting in an electrosurgical handpiece and a second end,
   (b) said second end having a generally transversely-extending portion terminating in an active, electrically conductive, tip portion tapering to a point,
   (c) said active tip portion being exposed electrically for applying electrosurgical currents to said nasal tissue when said shaft member first end is connected to a source of electrosurgical currents,
   (d) portions of said shaft member extending from the first exposed end to said transversely-extending portion adjacent said exposed tip portion being coated with an electrically insulating coating to prevent contact and passage of electrosurgical currents to areas adjacent to or surrounding the tissue to be excised,
   (e) the length of the exposed tip portion being greater than 0.05 but less than 0.30 inches.

2. An electrosurgical electrode for excising of nasal tissue as claimed in claim 10, wherein the diameter of the portion of the shaft member adjacent the second end is in the range of about 0.03–0.06 inches.

3. An electrosurgical electrode for excising of nasal tissue, comprising:
   (a) an electrically conductive shaft member having a first exposed end for mounting in an electrosurgical handpiece and a second end,
   (b) said second end having a generally transversely-extending portion terminating in an active, electrically conductive, tip portion tapering to a point, said tip portion being of brass,
   (c) said active tip portion being exposed electrically for applying electrosurgical currents to said nasal tissue when said shaft member first end is connected to a source of electro surgical currents,
   (d) portions of said shaft member extending from the first exposed end to said transversely-extending portion adjacent said exposed tip portion being coated with an electrically insulating coating to prevent contact and passage of electrosurgical currents to areas adjacent to or surrounding the tissue to be excised,
   (e) the length of said transversely-extending portion lying in the range of about 0.28–0.55 inches.

4. An electrosurgical electrode for excising of nasal tissue, comprising:
   (a) an electrically conductive shall member having a first exposed end for mounting in an electrosurgical handpiece and a second end,
   (b) said second end having a generally transversely-extending portion terminating in an active, electrically conductive, tip portion tapering to a point,
   (c) said active tip portion being exposed electrically for applying electrosurgical currents to said nasal tissue when said shaft member first end is connected to a source of electrosurgical currents,
   (d) portions of said shaft member extending from the first exposed end to said transversely-extending portion adjacent said exposed tip portion being coated with an electrically insulating coating to prevent contact and passage of electrosurgical currents to areas adjacent to or surrounding the tissue to be excised, the length of said shaft member being about 3 inches.

5. An electrosurgical electrode as claimed in claim 4, wherein the length of said shaft member coated with the electrically-insulating coating is about 2.04–2.42 inches.

6. An electrosurgical electrode as claimed in claim 5, wherein the transversely-extending portion extends at a right angle to the shaft member.

7. In combination:

electrosurgical apparatus capable of supplying high frequency currents, an electrosurgical handpiece having means at one end for connection to the electrosurgical apparatus and having at its opposite end means for holding an electrically conducive shaft member of an electrosurgical electrode and for supplying the high frequency currents to said electrode;

an electrosurgical electrode for performing nasal surgery, comprising:
   (a) an electrically conductive shaft member having a fast end mounted at the opposite end of the electrosurgical handpiece and a second end,
   (b) said second end having a generally transversely-extending portion terminating in an active, electrically conductive, tip portion, the length of said transversely-extending portion lying in the range of about 0.28–0.55 inches,
   (c) said active tip portion being exposed electrically for applying electrosurgical currents to patient nasal tissue when said shaft member is connected to a source of electrosurgical currents,
   (d) the portions of said shaft member extending to said transversely-extending portion adjacent said exposed tip portion being electrically insulating to prevent contact and passage of electrosurgical currents to areas adjacent to or surrounding the shaft member.

8. The combination of claim 7, wherein the high frequency currents are at a frequency exceeding 1.5 MHz.

* * * * *